United States Patent [19]

Arrang et al.

[11] Patent Number: 4,767,778

[45] Date of Patent: Aug. 30, 1988

[54] PHARMACEUTICAL COMPOSITIONS AND METHODS FOR STIMULATING $H_3$ HISTAMINE RECEPTORS

[75] Inventors: Jean-Michel Arrang, Gif; Monique Garbarg, Paris, both of France; Walter Schunack, Berlin, Fed. Rep. of Germany; Jean-Charles Schwartz, Paris, France; Ralph O. Lipp, Berlin, Fed. Rep. of Germany

[73] Assignee: Institut National de la Sante et de la Recherche Medicale (INSERM), Paris, France

[21] Appl. No.: 901,750

[22] Filed: Aug. 29, 1986

[30] Foreign Application Priority Data

Sep. 2, 1985 [FR] France ................................. 85 13024

[51] Int. Cl.[4] ........................................... A61K 31/415
[52] U.S. Cl. .................................................... 514/397
[58] Field of Search ........................................... 514/397

[56] References Cited

PUBLICATIONS

"Struktur–Wirkungs–Beziehungen bei Histaminanaloga, 20.Mitt. Absolute Konfiguration und histaminartige Wirkung der enantiomeren alpha-Methylhistamine", *Arch. Pharm.*, vol. 313, 1980, Gerhard et al., pp. 709, 714.

"Chiral Agonists of Histamine", *Frontiers in Histamine Research*, 1985, Schwartz et al, pp. 39–46.

*Primary Examiner*—Stanley J. Friedman
*Attorney, Agent, or Firm*—Young & Thompson

[57] ABSTRACT

The invention relates to a pharmaceutical composition containing histamine derivatives and to a method for treating diseases which involve histamine release and synthesis in the human or animal body.

9 Claims, No Drawings

PHARMACEUTICAL COMPOSITIONS AND METHODS FOR STIMULATING H3 HISTAMINE RECEPTORS

The present invention relates to the therapeutic application of histamine derivatives, and in particular of α-methylhistamine and its R stereoisomer, the optical rotation of which is laevorotatory and the configuration of which corresponds to that of L-histidine.

The two stereoisomers of α-methylhistamine were previously prepared as histamine analogs, but pharmacological study of these compounds had only enabled a very weak histaminic activity, which was similar for both stereoisomers, to be demonstrated in respect of the $H_1$ and $H_2$ receptors, the only receptors known at the time (Gerhard and Schunack, Arc. Pharm. (Weinheim) 1980, 313, 709). This observation led to the elimination of this product from a detailed pharmacological study and from any therapeutic application.

In fact, we have now discovered the powerful agonistic and highly stereoselective properties of α-methylhistamine in respect of a new class of receptors ($H_3$ receptors). Stimulation of the $H_3$ receptors mainly induces inhibition of the synthesis and release of histamine (Arrang. and al., Nature, 1983, 302, 832; Neuroscience, 1985, 15, 553; Frontiers in Histamine Research, C. R. Ganellin and J. C. Schwartz, eds., Pergamon Press, 1985, p. 143). We also found these properties in a few other compounds which are structurally close to α-methylhistamine and which are per se known in the literature.

Therefore an objet of the invention is a pharmaceutical composition which comprises a histamine derivative according to the formula

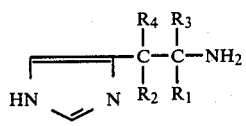

I in which each of $R_1$, $R_2$ and $R_4$ represents a hydrogen or a methyl, or $R_1$ and $R_2$ taken together represent a methylene, and $R_3$ is a hydrogen, a methyl or a carboxy, with the proviso that $R_1$, $R_2$, $R_3$ and $R_4$ are not simultaneously methyl groups, and a pharmaceutically acceptable carrier or diluent.

The invention is more particularly concerned with compositions containing the following examples of compounds:

1. α-methylhistamine or 4-(2-aminopropyl)-imidazole and its stereoisomers R(−) and S(+); (I:$R_1$=$CH_3$; $R_2$=$R_3$=$R_4$=H), see Gerhard and Schunack abaove.

2. α,α-dimethylhistamine or 4-(2-methyl 2-anino propyl)-imidazole (I:$R_1$=$R_3$=$CH_3$; $R_2$=$R_4$=H); disclosed by Schunack, Joint Meeting of the American chemical Society, Div. of Med. Chem, and the American Society for pharmacology and experimental therapeutic, Boston, USA, Aug. 18–22, 1985.

3. β-methylhistamine or 4-(1-methyl 2-amino ethyl)-imidazole and its stereoisomers (I:$R_2$=$CH_3$; $R_1$=$R_3$=$R_4$=H) disclosed by Ganellin and al. in J. Med. Chem. 1973, 16, 616 (racemic form) and by Schunack and al. in Frontiers in Histamine Research, C. R. Ganellin and J. C. Schwartz eds. Pergamon Press, 1985, p. 39 (stereoisomers).

4. β,β-dimethylhistamine or 4-(1,1-dimethyl 2-amino ethyl)-imidazole (I:$R_1$=$R_3$=H; $R_2$=$R_4$=$CH_3$), disclosed by Dwart and al., J. Med. chem. 1976, 19, 923.

5. 2-(4-imidazolyl)-cyclopropylamine (I:$R_1$-$R_2$=$CH_2$; $R_3$=$R_4$=H), disclosed by Burger and al. J. Med. Chem. 1970, 13, 33.

6. α-methylhistidine and its stereoisomers (I:$R_1$=$CH_3$; $R_3$=COOH; $R_2$=$R_4$=H), disclosed by B. Robinson and T. M. Shepherd J. Chem. Soc. 1961, 5037-8.

Pharmacological Investigation

The effect of the histamine derivatives according to the invention on the $H_3$ autoreceptors which control the release of ($^3$H) histamine induced by depolarization of slices of rat brain was studied according to the method described by Arrang. and al. (Nature, 1983, 302, 832-837). The derivatives behave as complete agonists of the $H_3$ receptors and produce a maximal inhibition of release identical to that induced by histamine (approximately 60%). The 50% effective concentration of the R (−) isomer of α-methylhistamine is 2±1 nM, which corresponds to an activity relative to histamine ($EC_{50}$=60±10 nM) of approximately 3,000%; in contrast, the S (+) isomer has an $EC_{50}$ of 700±300 nM and an activity relative to histamine of 9% (stereoselectivity factor 350).

The effect of α-methylhistamine, like that of histamine, is reversed by various $H_3$ antagonists, such as impromidine (see Table 2 below).

In contrast, the histamine derivatives as already shown for the two isomers of α-methylhistamine are of very low activity in respect of the $H_1$ and $H_2$ receptors, on which their activity relative to histamine is from 0.5 to 2% (Schunack and al., Frontiers in Histamine Research, C. R. Ganellin and J. C. Schwartz eds., Pergamon Press, 1985, 39). Given the greater sensitivity of the $H_3$ receptors to the agonists, the outcome is that the R isomer stimulates these latter at concentrations approximately 10,000 to 100,000 times lower than those at which it stimulates the $H_1$ and $H_2$ receptors. It hence constitutes the first highly selective agonist of the $H_3$ receptors. The results are set in Table 1 below.

TABLE 1

Inhibition of the release of ($^3$H) histamine using slices of rat cerebral cortex.

| Ex. No. | $EC_{50}$ (nM) | Activity relative to histamine (%) | |
| --- | --- | --- | --- |
| | | $H_3$ receptors | $H_1$/$H_2$ receptors |
| 1 (R) | 2 ± 1 | 3,000 | 0.5–1 |
| 1 (S) | 700 ± 300 | 9 | 0.5–2 |
| 2 | 20 ± 10 | 300 | <1 |
| 3 (R, S) | 20 ± 5 | 120 | 2–2 |
| 4 | 50 ± 20 | 120 | <0.1 |
| 5 | <100 | >60 | <1 |
| 6 (R, S) | 1000 ± 500 | 6 | inactive |

TABLE 2

Inhibition by α-methylhistamine of the release of ($^3$H) histamine, using slices of rat cerebral cortex.

| Conditions | Release of ($^3$H) histamine induced by 30 mM K$^+$ (% of the total) |
| --- | --- |
| Controls | 16 ± 1 |
| (R)-α-methylhistamine (100 nM) | 6 ± 1 *(−63%) |
| (R)-α-methylhistamine (100 nM) + | 14 ± 2 N.S. |

TABLE 2-continued

Inhibition by α-methylhistamine of the release of
($^3$H) histamine, using slices of rat cerebral cortex.

| Conditions | Release of ($^3$H) histamine induced by 30 mM K$^+$ (% of the total) |
|---|---|
| impromidine (100 μM) | |

*p < 0.01
N.S. not significant

The effect of α-methylhistamine was also studied on the H$_3$ autoreceptors which control the synthesis of histamine in slices of rat brain, according to Arrang. and al., 1985, in Frontiers in Histamine Research, C. R. Ganellin and J. C. Schwartz eds., Pergamon Press, p. 143. α-Methylhistamine induces the same maximal inhibition as histamine (approximately 70%) of the stimulation by potassium of the synthesis of ($^3$H) histamine, with a relative activity of the same order as in the release model. Its effect is reversed competitively by H$_3$ antagonists such as burimamide (see Table 3 below).

α-Methylhistamine also inhibits the synthesis of histamine in slices of human cerebral cortex and that of posterior hypothalamus (mamillary), by stimulation of the H$_3$ receptors.

TABLE 3

Inhibition by α-methylhistamine of the potassium induced synthesis of ($^3$H) histamine in slices of rat cerebral cortex.

| Conditions | Stimulation of synthesis of ($^3$H) histamine induced by 30 mM K$^+$ (%) |
|---|---|
| Controls | 85 ± 4 |
| (R, S)-αmethylhistamine (100 nM) | 40 ± 4 *(−53%) |
| (R, S)-αmethylhistamine (100 nM) + burimamide (10 μM) | 90 ± 5 N.S. |

*p < 0.01
N.S. not significant

To study in vivo the effect of (R)-α-methylhistamine on the synthesis of histamine, the method of Verdiere and al., (Brain Research, 1977, 129, 107) was used with slight modifications.

The rats received 200 μCi of ($^3$H)-L-histidine (i.v.) and the ($^3$H) histamine synthesized is measured 10 minutes later (see Table 4 below).

The simultaneous administration of (R)-α-methylhistamine (10 mg/kg) significantly reduces the synthesis of ($^3$H) histamine in the brain and also in the peripheral tissues studied. Since this effect is completely reversed by an antagonist of the H$_3$ receptors, it results from stimulation of these receptors.

TABLE 4

Inhibition by (R) α-methylhistamine of the synthesis of ($^3$H) histamine in rats in vivo.

| | ($^3$) histamine (% of the total radio-activity × 10$^{-3}$) | | Variation |
|---|---|---|---|
| Tissue | Controls | Treated | (%) |
| Cerebral cortex | 95 ± 6 | 53 ± 6 | −45** |
| Hypothalmus | 272 ± 11 | 185 ± 32 | −32** |
| Lungs | 138 ± 10 | 94 ± 10 | −32* |
| Spleen | 60 ± 8 | 42 ± 5 | −30* |
| Kidneys | 53 ± 4 | 37 ± 5 | −30* |

*p < 0.05
**p < 0.01

The animals (6-13) received an intravenous injection of 200 μCi of ($^3$H)-L-histidine alone (controls) or with (R)-α-methylhistamine, 10 mg/kg (treated), and were sacrificed 10 minutes later.

The ($^3$H) histamine extracted from the tissues with HClO$_4$ was isolated.

Thus, the histamine derivatives of formula I powerfully inhibit the release and synthesis of histamine by very selectively stimulating the H$_3$ receptors. In consequence, they are likely to decrease histaminergic transmission in the digestive tract and in the nervous, cardiovascular and immune systems. They can be used in therapy as a drug having sedative effects, as a sleep regulator, anticonvulsant, regulator of hypothalamo-hypophyseal secretion, antidepressant, modulator of cerebral circulation, and the like.

Furthermore, inhibition of the release of inflammation messengers in various allergic conditions (e.g. asthma) is expected to result from the stimulation of the H$_3$ receptors of the lung, for example.

In gastroenterology, the inhibition of release of gastric histamine is likely to exert antisecretory and antiulcerative effects. Modification of release of the messengers of immune responses is likely to modulate the latter responses.

By virtue of these novel and unexpected properties, the histamine derivatives of formula I and particularly α-methylhistamine, mainly in the form of its R stereoisomer, may be used for treating diseases which involve histmine synthesis and release in the human or animal body. Thus, the invention provides a method for treating a patient suffering from such a disease by administering a therapeutically effective amount of a histamine derivative of formula I. From their mode of action, their diverse pharmacological effects and their low toxicity in animals, applications of these derivatives may be predicted both in human and veterinary medicine, at doses of the order of 0.1 to 10 mg/kg administered, in particular, orally or parenterally.

They can be presented, in particular, in the form of tablets, dragees, gelatine capsules, aerosols, injectable solutions or suppositories, for example in unit doses containing 10 to 50 mg of a compound (I).

What is claimed is:

1. A method of selectively stimulating H$_3$ histamine receptors in a patient in need thereof, comprising administering to said patient an effective amount of a compound of the formula $$\begin{array}{c} R_4 \ R_3 \\ | \ \ | \\ \boxed{\phantom{xxx}}\text{—C—C—NH}_2 \\ | \ \ | \\ HN \diagdown N \ \ R_2 \ R_1 \end{array}$$

in which R$_1$, R$_2$, R$_3$ and R$_4$ are each hydrogen or methyl, and at least one but not more than two of R$_1$, R$_2$, R$_3$ and R$_4$ are methyl, or two of R$_1$, R$_2$, R$_3$ and R$_4$ are together methylene, said amount being effective to selectively stimulate H$_3$ histamine receptors.

2. Method according to claim 1, wherein said compound is α-methylhistamine.

3. Method according to claim 2, wherein said α-methylhistamine is (R)-α-methylhistamine.

4. Method according to claim 1, wherein said amount is 0.1 to 10 mg/kg of a said patient.

5. Method according to claim 1, wherein said amount is 10 to 50 mg per unit dose.

6. A pharmaceutical composition for selectively stimulating $H_3$ histamine receptors in a patient in need thereof, comprising an effective amount of a compound of the formula

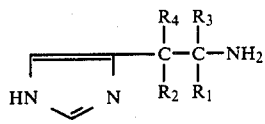

in which $R_1$, $R_2$, $R_3$ and $R_4$ are each hydrogen or methyl, and at least one but not more than two of $R_1$, $R_2$, $R_3$ and $R_4$ are methyl, or two of $R_1$, $R_2$, $R_3$ and $R_4$ are together methylene, said amount being effective to selectively stimulate $H_3$ histamine receptors, in admixture with a pharmaceutically acceptable excipient.

7. Pharmaceutical composition according to claim 6, wherein said compound is α-methylhistamine.

8. Pharmaceutical composition according to claim 7, wherein said α-methylhistamine is (R)-α-methylhistamine.

9. Pharmaceutical composition according to claim 6, said composition being in dosage unit form adapted for administration to obtain an $H_3$ histamine receptor-stimulating effect, comprising from about 10 to about 50 mg of a said compound per dosage unit.

* * * * *